(12) United States Patent
Dick et al.

(10) Patent No.: US 8,469,902 B2
(45) Date of Patent: Jun. 25, 2013

(54) DETERMINING A JOINT ORIENTATION FOR AN IMPLANTATION

(75) Inventors: Robert Dick, München (DE); Lars Dohmen, München (DE)

(73) Assignee: Brainlab AG, Feldkirchen (DE)

( * ) Notice: Subject to any disclaimer, the term of this patent is extended or adjusted under 35 U.S.C. 154(b) by 1594 days.

(21) Appl. No.: 11/955,096

(22) Filed: Dec. 12, 2007

(65) Prior Publication Data
US 2008/0287962 A1  Nov. 20, 2008

Related U.S. Application Data

(60) Provisional application No. 60/882,760, filed on Dec. 29, 2006.

(30) Foreign Application Priority Data

Dec. 12, 2006  (EP) ..................................... 06025672
Dec. 11, 2007  (EP) ..................................... 07122947

(51) Int. Cl.
*A61B 5/00* (2006.01)
(52) U.S. Cl.
USPC ....................................................... 600/595
(58) Field of Classification Search
USPC ................................................ 600/587, 595
See application file for complete search history.

(56) References Cited

U.S. PATENT DOCUMENTS 6,205,411 B1  3/2001  DiGioia, III et al.

FOREIGN PATENT DOCUMENTS

| DE | 197 09 960 | 9/1998 |
| EP | 1 402 855 | 3/2004 |
| WO | 02/080824 | 10/2002 |

*Primary Examiner* — Max Hindenburg
(74) *Attorney, Agent, or Firm* — Renner, Otto, Boisselle & Sklar, LLP

(57) ABSTRACT

A method for determining an orientation of an artificial joint, in particular for planning an implantation of at least one artificial joint in a human or animal body, wherein a first part of the artificial joint and a second part of the artificial joint are designed to be able to form an artificial joint connection with each other, wherein the first part is provided for implantation in a first body structure of the human or animal body, and the second part is provided for implantation in a second body structure of the human or animal body, in order to replace an anatomical joint which connects or connected the first body structure to the second body structure, wherein the method comprises the following steps:
  body structure data are provided which describe a mobility of the first body structure relative to the second body structure;
  an orientation which is suitable for implanting the artificial joint is determined on the basis of the body structure data.

21 Claims, 3 Drawing Sheets

DETERMINING A JOINT ORIENTATION FOR AN IMPLANTATION

RELATED APPLICATION DATA

This application claims priority of U.S. Provisional Application No. 60/882,760 filed on Dec. 29, 2006, which is incorporated herein by reference in its entirety.

FIELD OF THE INVENTION

The present invention relates to determining an orientation of an anatomical joint and/or an orientation of an artificial joint which is suitable for implanting the artificial joint, in particular planning the implantation of an artificial joint, and to a device for determining the orientation for implanting an artificial joint.

BACKGROUND OF THE INVENTION

An artificial joint is typically implanted to replace a joint already present in the human or animal body. In the following, this joint to be replaced is called an anatomical joint. The anatomical joint may be defective for any one of a number of different reasons, such as, for example damage from an accident or illness (e.g., osteoporosis), restricted functionality, pain. In order to minimize complications after the implantation of the artificial joint, an implantation of the artificial joint with a suitable orientation is advantageous.

SUMMARY OF THE INVENTION

The artificial joint, which in accordance with the invention is intended to replace an anatomical joint such as for example a hip joint or a knee joint, ankle, knuckle or shoulder joint, preferably has at least two parts that can be moved relative to each other and can form a joint connection. An example of a (first) part of an artificial joint is a joint cavity, and an example of the corresponding (second) part is a joint head, which, for example, is attached to a shaft. The head and the cavity are designed so as to fit each other. The first part, for example, can be the Joint cavity, and the second part can be the joint head. The terms "first" and "second" here are arbitrary and can also be selected the other way round. They merely express that a joint has two cooperating parts.

The first part of the artificial joint is preferably designed to be implanted in a first body structure (for example a bone or cartilage or a mixture of these). An artificial joint cavity, for example, can be implanted in a pelvic bone, wherein the artificial joint cavity represents the first part and the pelvis represents the first body structure. Also, in a total endoprosthesis, the artificial ball joint head can be implanted together with a shaft in a femur, wherein, for example, the ball joint head together with the shaft represents the second part of the artificial joint, and to the femur represents the second body structure.

An implant dataset is preferably, but not compulsorily, provided in accordance with the invention. The implant data set, for example, can be stored in a memory or input via an input interface (for example a network connection, keyboard, etc.). The implant dataset preferably includes data relating to a mobility of the first part relative to the second part.

The term "mobility" is illustrated in the following on the basis of the artificial joint, but also applies analogously to the anatomical joint, wherein the first part of the artificial joint corresponds to the first body structure and the second part of the artificial joint corresponds to the second body structure. In particular, the term includes a range of motion by the artificial joint, e.g., the possible angles that the first part of the artificial joint can adopt relative to the second part, in particular the maximum possible angles. These angles can be defined for planes that, for example, are perpendicular to each other and which can represent characteristic planes (key planes) of the artificial joint. They can represent maximum ranges of movement that the artificial joint allows. Within the framework of a relative movement, the second part (e.g., the sphere together with a shaft), for example, can come to abut against the first part (e.g., the cavity). The ranges of movement, for example, can be described by angles that are defined for particular planes, in which a movement of the first part relative to the second part is possible. Mobility also can include possible locations, in particular extreme locations or key locations, at which the first part adopts a particular location, in particular extreme location or key location, relative to the second part. An example of an extreme location is given when the first part has reached the perimeter of a possible range of motion relative to the second part, and the two parts abut against each other, such that only a movement in one direction is still possible, away from the extreme location (point of abutment) and back to a relative location already previously adopted, within the framework of a normal joint movement. A normal joint movement is one in which the two parts of the joint (the first and second part) are not separated, but rather perform movements that correspond to the (healthy) movements of the anatomical joint. The locations, for example, can be described in a reference system that is anchored in the first or second part and for example described using Cartesian coordinates or spherical coordinates or angles relative to the planes. The relative locations can be described by symmetry axes or symmetry planes in the first part relative to symmetry axes or symmetry planes in the second part, or the positions of particular elements (e.g., landmarks) of the first part relative to positions of particular elements of the second part (for example the lowest point of a cup-shaped recess in a cavity joint).

The implant dataset can also include data concerning the geometry of the anatomical joint. Data concerning the geometry, for example, can include data concerning the shape and/or configuration of the artificial joint. Mobility can be affected by the geometry and/or by the material or materials that the artificial joint comprises or from which it is formed, in particular the elasticity, flexibility and/or rigidity of the materials. The latter properties and/or the geometry can affect the forces at which the parts of the artificial joint (the first and second part) can be separated from each other. Mobility also preferably includes information concerning a possible relative movement of the first and second part in the normal case in which the artificial joint imitates a movement of the healthy anatomical joint. Mobility also preferably includes information concerning a movement of the first part relative to the second part, in which the first part separates from the second part, as is particularly undesirable and as may be the case in the event of a luxation. This undesirable relative movement may be affected by the geometry of the artificial joint. The geometry affects the degree of resistance that the artificial joint offers against an undesirable separation of the first and second part.

The implant dataset preferably also includes data concerning the inhibition of a movement that causes a separation of the first part and the second part, e.g., the inhibition of a luxation movement. In particular, the implant dataset includes data concerning the degree of inhibition of such a movement or concerning the resistance offered to such a movement. The degree of inhibition and/or resistance can follow from the geometry of the artificial joint and can be expressed by geometric properties, as discussed in more detail further below. It can also be expressed by forces, for example friction forces or holding forces.

The implant dataset, for example, can be obtained from a database that stores the corresponding data for the individual types of implants. The properties of the implant also can be measured, for example, by relative movements being performed between the first and second part and by attempting at a position (e.g., a key position) or at particular relative positions of the first and second part, to separate the first part from the second part and measuring the corresponding forces needed to perform the separation. These forces then can be added as data to the implant dataset and/or can form the implant dataset.

In accordance with one aspect of the invention, body structure data are preferably provided that are patient-specific. The data can include information concerning a mobility of the anatomical joint, e.g., a mobility of the first and/or second body structure, wherein the term "mobility" is understood analogously to the term mobility as illustrated above and includes information concerning possible relative movements and/or relative locations of the first body structure relative to the second body structure.

The body structure data preferably include information concerning the location of the first body structure and/or second body structure, in particular concerning a relative orientation of the first body structure relative to the second body structure. The location and/or orientation can be described in a predetermined reference system, for example in a reference system of the patient, in a reference system of a navigation system (e.g., a reference system in which a detection means, for example a camera of the navigation system, lies), in a reference system in which the operating theater lies, or in a reference system which lies in one of the body structures. If, for example, the information concerning the location includes both information concerning the location of the first body structure and information concerning the location of the second body structure, then the location of at least one of the two body structures can be described in a reference system in which the other body structure lies.

The body structure data, which relate to the mobility of the first body structure relative to the second body structure, can include at least one range of motion of the anatomical joint, e.g., relative movements of the first body structure relative to the second body structure. In particular, the body structure data can include at least one maximum possible range of motion, in particular two ranges of movement. The ranges of movement are preferably described for particular movement directions and/or movement planes. In the case of a hip joint implant, the ranges of movement, for example, can be described in the direction of the extension/flexion of the anatomical joint and/or in the direction of the adduction and abduction of the joint. In particular, the mobility can include one or more particular key locations of the first body structure relative to the second body structure. For example, a specification concerning an extreme location and/or a maximum abduction angle between the first body structure (joint cavity) and the second body structure (joint head), in order to calculate or estimate the risk of a possible luxation for this scenario, as further discussed below.

The body structure data can include data concerning angles and/or angular ratios. The angles can be provided by moving the first body structure relative to the second body structure. The angular ratios can be provided by referring to a neutral relative location between the first body structure and the second body structure. The body structure data depend on the orientation of the anatomical joint. In particular, the body structure data allow the orientation of the anatomical joint to be calculated, if the angle between the movement end points is additionally incorporated into the calculation. The body structure data can include data that are a function of the orientation of the anatomical joint. The angular ratios, which are further described below, represent an example of such data, since the angular ratios would change depending on the orientation of the anatomical joint. The absolute angular values, which are also further described below, represent additional examples. The body structure data can thus include both data which represent a function of the orientation of the anatomical joint, but also data which directly represent the orientation of the anatomical joint. One example of this is the center point of the range of motion, further described below.

The information concerning the mobility also can include data concerning the geometry of the anatomical joint, in particular data concerning the configuration and/or shape of the anatomical joint. These data can be obtained by diagnostic methods, such as for example magnetic resonance recordings, x-ray recordings, computer tomography (CT) recordings, etc. Information concerning the mobility can include data concerning the inhibition of a movement and/or the resistance against a movement of the first and/or second body structure. The term mobility can include data concerning ligament tensions, and the location of ligaments and tissue structures which effect the movement and range of motion of the anatomical joint. Typical (normal) values can be contained in the data concerning the mobility, for example typical values concerning the resistance against a luxation and/or typical values concerning ranges of movement, such as for example typically (normally) obtain for a human being.

An orientation of the anatomical joint, which can be used for planning the implantation of the artificial joint and in particular allows an orientation of the artificial joint that is suitable for the implantation to be determined, is preferably determined on the basis of body structure data (in accordance with the invention, the orientation of the anatomical joint can be determined). This determined orientation then can be used by a planning method or a physician to plan an implantation, in particular in order to determine a suitable location and/or orientation of the artificial joint. In accordance with the invention, a suitable orientation of the artificial joint also can be directly determined from the body structure data, for example, by comparing ranges of movement of the anatomical joint and the artificial joint, without determining the orientation of the anatomical joint. Determining the orientation of the anatomical joint, however, also cam be an intermediate step for determining the suitable orientation of the artificial joint.

The determined orientation of the anatomical joint then can be used as a reference point for an orientation of the artificial joint that is suitable for the implantation. The implantation can be planned such that the orientation of the artificial joint matches the determined orientation of the anatomical joint. Matching, however, is not compulsory, particularly if an orientation of the artificial joint that deviates from the anatomical joint is desirable for medical reasons.

The suitable orientation of the artificial joint is preferably also determined on the basis of the at least one implant dataset, wherein the determined orientation of the artificial joint is suitable for an implantation of the first and/or second part of the artificial joint in a body structure. The orientation is in particular suitable for an implantation of the first part of the artificial joint (e.g., the artificial joint cavity) in a first body structure (e.g., the pelvic bone) and/or for an implantation of a second part of the artificial joint (e.g., a sphere together with a to shaft) in a second body structure (e.g., the femur).

The suitable orientation, for example, can be described as a straight line or as a vector in different reference systems, such as have already been discussed herein in connection with the location of the first and second body structure. The suitable orientation can be described in a reference system in which the patient lies, or in which the operating theater lies, or in which a navigation system and/or its detection system lies. The suitable orientation of the artificial joint also can be described in a reference system in which the first body structure or the second body structure lies or in which one of the parts of the artificial joint lies. The suitable orientation can be specified by referring to symmetry planes or landmarks of the first and/or second body structure, such as for example the symmetry planes of the pelvic bone.

The orientation of a joint is preferably determined via its mobility, in particular its range of motion, and/or its symmetry properties (e.g. its symmetry axes, symmetry points or symmetry planes, in particular the longitudinal axes of a part of the joint).

The orientation, for example, can be described by a vector which has its origin in the center of the base of the cup-shaped recess in the acetabulum. Alternatively, the vector can have its origin where the rotational point of the anatomical joint is situated.

The orientation of a joint, in particular the anatomical joint and/or the artificial joint, for example, can be determined as follows. One part of a two-part joint can be fixed, while the other part travels the perimeter of the joint's permissible range of motion. This inherently closed perimeter line of the range of motion can then be assigned a center point. Alternatively, one part of the joint can be moved along two main axes which are in particular orthogonal to each other, and the intersection point of these main axes is defined as the center point of the range of motion. The aforesaid centre point of the range of motion, together with the centre point of the joint (which in particular remains stationary during a relative movement of the parts of the joint), then spans a straight line which represents the orientation of the joint.

If the location of the center point of the rotational joint is not known, the orientation, for example, can be determined such that the perimeter of the range of motion spans a plane, and a center axis of the range of motion is normal to this plane and passes through the center point of the area described by the perimeter. The joints also can be moved along a main movement direction, wherein these directions can be perpendicular to each other. The planes spanned by the movement intersect, and the intersection line can be defined as the orientation of the joint.

The mobility of the first anatomical body structure relative to the second anatomical body structure, and thus the mobility of the anatomical joint, is in particular described in accordance with one of the following variants:
  a) by the center point of a range of motion which results from the movement of the first part of the anatomical joint relative to the second part of the anatomical joint, wherein in order to define the orientation, the center point is in particular connected to another point that does not change its location during the movement for determining the range of motion, in particular the rotational point, such that a line results which describes the orientation of the anatomical joint;
  b) by specifying absolute angles of the flexion and/or extension and/or abduction and/or adduction, wherein the middle of the extension/flexion angular range and/or the middle of the abduction/adduction angular range is preferably used, so as to define the orientation. Alternatively or additionally, the neutral relative location of the anatomical joint can also be determined (see below);
  c) by the ratio of angles that describe the joint movement angular ranges relative to a neutral relative location in which the body structures assume a predetermined relative location, for example the ratio of the flexion angle to the extension angle of the anatomical joint and/or the ratio of the abduction angle to the adduction angle. The orientation of the anatomical joint depends on the neutral relative location and the angular ratios. If, for example, the orientation of an implant joint is described by the center axis of the range of motion of the implant joint, then by using the aforesaid information, it is possible to determine how the center axis will have to be changed so that the desired angular ratios are set when the body structures are in the neutral relative location, if the artificial joint replaces the anatomical joint.

The aforesaid angles and/or angular ratios are preferably determined before the operation or inter-operatively by analyzing the range of motion (ROM). As an alternative to or in addition to the aforesaid determination, it is also possible (in particular when defining the angular ratios) to define the orientation based on a statistical study. A preferred angular ratio for the flexion to the extension and/or for the abduction to the adduction, for example, can follow from the statistical study. The orientation of the artificial joint can thus be determined without performing an advance motion analysis.

The data concerning the mobility of the artificial joint then can include data relating to the orientation of the artificial joint, e.g., data concerning the range of motion, in particular the angular ranges of the flexion, extension, abduction, adduction and/or preferably data concerning the ratios of the flexion angle to the extension angle and/or of the abduction angle to the adduction angle. The inventors have in particular found that using the ratios as a basis for determining a suitable orientation represents a particularly easy-to-manage and nonetheless reliable initial basis for determining the orientation.

The method in accordance with the invention takes into account the position of one part of the joint relative to the other part of the joint. Thus, for example, when implanting a hip joint, the relationship of the shaft relative to the cavity can also be taken into account when positioning the implant.

As discussed above, a centre point of the joint (which is stationary during the relative movements) can be determined from the range of motion and in particular the relative locations between the first and second body structure. This centre point can be adduced in order to determine a suitable location for implanting the artificial joint, i.e. it is possible to determine the location which the rotational point of the artificial joint should adopt. This location can in particular be selected such that it matches the rotational joint centre point of the anatomical joint. The suitable location can thus be determined by the spatial position of the rotational joint centre point, i.e. in one of the aforesaid reference systems.

The suitable orientation is preferably determined under particular ancillary conditions, such as for example that the range of motion of the artificial joint includes or at least approximately corresponds to the range of motion of the anatomical joint. "At least approximately" means that if the range of motion is described by angles, a deviation of the two ranges of motion from each other is smaller than 20 degrees, in particular smaller than 10 degrees, 5 degrees or 2 degrees. This ensures that movements of the first body structure relative to the second body structure cannot abut the limits of the possible range of motion of the artificial joint. Such an abutment can cause complications. The artificial joint is preferably positioned such that the orientation of the artificial joint (in particular the center axis of a possible range of motion of the artificial joint, e.g., a plane of the movement) at least approximately matches the orientation of the anatomical joint, e.g., the center axis of the range of motion of the anatomical joint (in a corresponding plane), wherein "at least approximately" is intended to mean that a deviation of the center axes from each other is smaller than 20 degrees, in particular smaller than 10 degrees, in particular smaller than 5 degrees, in particular smaller than 2 degrees of the possible range of motion. At a maximum range of motion of the artificial joint of 100 degrees, this would mean for the latter example of 2 percent that the deviation of the center axis of the range of motion of the artificial joint from the center axis of the range of motion of the anatomical joint is less than ±2 degrees. The center axis passes through the center point of the joint and through the center point of the range of motion.

As an alternative to or in addition to the aforementioned ancillary condition for determining the suitable orientation on the basis of the ranges of motion of the anatomical and the artificial joint, the suitable orientation also can be determined as shown in the following, wherein the suitable location is determined on the basis of the implant dataset which contains information concerning the resistance or the risk of a luxation. In particular, the implant dataset contains information concerning a separation of the first part from the second part for particular locations of the first part relative to the second part. A value for a resistance against an undesirable separation is preferably taken into account when to determining the suitable orientation. This predetermined value of a resistance or desired resistance can be orientated on the typical resistance of an anatomical joint against a luxation in a predetermined relative location of the first body structure relative to the second body structure. The resistance value can be taken from an anatomical database. In particular, the resistance value can be selected such that it matches or at least approximately matches a typical anatomical value for a resistance, wherein the term "at least approximately" and the associated deviations from the typical value may be understood in the sense defined above and, for example, may be less than 20 percent. An anatomical value for a resistance can be determined in experiments and can be interpreted such that it corresponds to a counter-pressure with which an intact capsule and the ligaments of the acetabulum oppose a luxation.

The anatomical data, in particular the data concerning the relative locations of the first and second body structure and/or possible ranges of motion, are preferably compared with anatomical data from a database which describe normal (typical) or maximum possible ranges of motion and/or relative locations such as (normally) obtained in a human being or a particular animal. In this way, a plausibility test can performed on the input anatomical data. A warning signal can be output if the test reveals that the data deviate from the normal data and/or are not within a normal range of values.

Preferably, at least one suitable orientation is determined, i.e., it is also possible to determine more than one suitable orientation. The term "at least one orientation" also includes determining ranges for a suitable orientation. Examples of ranges are angular ranges (e.g., in relation to symmetry planes) within which an implantation of an artificial joint is regarded as being suitable. A plurality of angles or an angular range, for example, can be suitable for implanting an artificial joint in that the maximum possible angular range of movement of the anatomical joint is within the maximum possible angular range of movement of the artificial joint. Such a plurality of orientations or such orientation ranges can be output by means of a display means (e.g., a monitor) or generally by means of a user interface, such that an operator, in particular a surgeon, can select an orientation from the proposed locations or can select an orientation from within the proposed orientation range. The plurality of orientations or the orientation ranges also can be restricted, and/or reduced to one suitable location, on the basis of other ancillary conditions, such as for example minimizing the risk of a luxation (see above).

A plurality of implant datasets can be provided, wherein each implant dataset relates to a different artificial joint. The different artificial joints can exhibit different mobilities. A suitable artificial joint (together with the implant dataset corresponding to it) or a plurality of suitable artificial joints (together with the implant datasets corresponding to them) can then be selected on the basis of the anatomical data.

Preferably, an artificial joint is selected for which the maximum possible range of motion is greater than the maximum possible range of motion of the anatomical joint to be replaced. It can be selected automatically, or proposals, for example, can be submitted to a user, who can then make the final selection.

The method described above for determining an orientation can be used in a planning method in accordance with the invention for planning an implantation of an artificial joint. An operator, for example a surgeon, can determine an orientation that is suitable for an implantation based on the implant dataset and the body structure data in accordance with the method described herein, and can thus plan the implantation of the artificial joint on the basis of the suitable orientation. The orientation is preferably determined such that after the artificial joint has been implanted with the suitable orientation, the implanted joint can adopt any locations of the first part relative to the second part that the first and second body structure were also able to adopt on the basis of the anatomical joint.

The aforesaid methods can be implemented as a program that is stored on a computer-readable storage medium (for example a CD or DVD) or can be transmitted via a signal wave (for example as an internet download transmission).

The present invention also relates to a device for determining an orientation of an anatomical joint and/or an orientation of the artificial joint that is suitable for an implantation. The device can include a memory for storing the at least implant dataset and for storing the body structure data. The device also can include a data processing means designed to perform steps of the aforesaid method, in particular in order to determine or calculate the orientation of the anatomical joint and/or the suitable orientation of the artificial joint. Numerical methods and/or analytical methods can be used by the processing means to mathematically determine the orientation (of the anatomical and/or the artificial joint) based on the body structure data and preferably also based on the at least one implant dataset. If a plurality of implant datasets are available, the implant datasets preferably are first restricted, for example to one implant dataset, as has already been described above. In a following calculation process (or step), the orientation (of the anatomical and/or the artificial joint) then can be determined, wherein the selected implant dataset is used which corresponds to the selected artificial joint.

The device preferably also comprises a detection means for at least partially determining the body structure data, wherein the detection means is preferably designed such that it can detect marker means attached to the first and/or second body structure. In this way, when the first body structure moves relative to the second body structure (or vice versa), it is possible to determine the range of motion and/or possible locations of the first body structure relative to the second body structure. The data thus obtained then can be used as body structure data in determining the orientation (of the anatomical and/or the artificial joint).

The device is preferably designed such that it comprises a user interface, in particular an indicating means (for example a screen), which is designed to indicate to the user when at least one of the two body structures (the first and second body structure) moves. The indicating means is in particular designed such that it indicates to the user movements of the body structures that are still outstanding and/or indicates to the user the directions in which the movements are to be performed. If, for example, only a movement in an extension/flexion direction has hitherto been performed, the indicating means (e.g., screen) can indicate to the operator that a movement in an abduction/adduction direction is still outstanding, in order to have sufficient body structure data for determining an orientation. In particular, the operator can be required to input when a relative location between first body structure and a second body structure represents an extreme location or key location that, for example, corresponds to the perimeter of a possible range of motion of the first body structure relative to the second body structure.

BRIEF DESCRIPTION OF THE DRAWINGS

The forgoing and other features of the invention are hereinafter discussed with reference to the drawings.

DETAILED DESCRIPTION

Figure 1A:
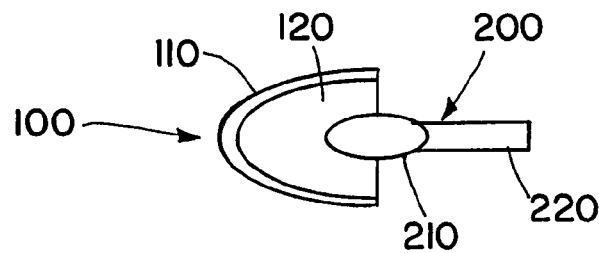
FIGS. 1a-1c illustrates the range of motion of an artificial joint.

In the following detailed description, a hip joint is described as an example of an anatomical joint, wherein the range of motion of the hip joint, more specifically the given range of motion of the (anatomical) hip joint of a patient, is used to determine a suitable orientation of the artificial joint.

During a surgical operation for a total endoprosthesis of a hip joint, the two parts of the anatomical hip that move the anatomical joint are replaced with two parts of an artificial joint (a two-part implant). The acetabulum (joint cavity) within the pelvic bone (pelvis) is replaced with a joint cavity implant. The proximal part of the femur is replaced with an implant combination consisting of a shaft and a joint head, which in the following is called the shaft implant. In most cases, the shaft is inserted into the proximal femur, while the joint head is placed onto the shaft.

The success of the surgical operation depends on the stability of the implanted artificial joint in the bone (pelvis or femur, respectively) and also depends on the range of motion permitted by the new artificial joint. The range of motion can affect the stability. A range of motion that is too small causes one part of the artificial joint to abut against the other part of the artificial joint and can consequently result in the stability of the implant, i.e., the connection between the implant and the bone, being impaired. This can result in the implant becoming loose or completely detaching from the bone. The associated complications for the patient are include a limited range of motion, pain, the risk of a dislocation and the risk of prematurely having to undergo another operation.

The device and method in accordance with the present invention assists the surgeon in finding an optimum orientation of the artificial joint, in particular the artificial joint cavity and/or the artificial joint head, in order to thus obtain an optimum range of motion. The range of motion of the anatomical joint preferably forms the basis for determining the most optimum possible orientation and in particular for positioning the artificial joint. This range of motion of the anatomical joint can be provided as a dataset, determined before the surgical operation or determined during the surgical operation. On the basis of the data concerning the range of motion (ROM), the location of the artificial joint cavity and/or the artificial shaft implant, i.e., the two parts of the implant, is then determined, and the positioning using the suitable orientation is planned and performed, in particular positioning during the surgical operation using the orientation that has been determined to be suitable.

It is not necessary to orientate oneself on planes of the pelvis when determining the suitable orientation, although this can of course also be performed. If one orientates oneself on the planes of a pelvis, then two angles are defined that relate to the planes of the pelvis, namely the inclination and the anteversion. A so-called safe zone for implanting an artificial joint cavity is defined in the literature. This safe zone is for example 40 degrees to 60 degrees for the inclination and 10 degrees to 30 degrees for the anteversion. The zones are selected such that the probability of an error in orientation is minimized. The values specified, however, are only statistical values and are not adapted to the given anatomy of the individual patient. This can result in an implantation, orientated on the values of the safe zone, which may not be the optimum implantation for an individual patient. It is also useful to determine the planes, in particular the symmetry planes, of the pelvis. This can be difficult if the patient is situated in a lateral position, since it is preferable to detect a point (the ASIS point) in the anterior-superior area of the contralateral iliac spine. If the individual range of motion of the anatomical joint (of a particular patient) is taken into account, then it is possible to avoid or reduce undesirable and in particular painful tensions of the ligaments. Preferably taking into account the individual anatomical range of motion of the anatomical joint allows relative extreme locations of the two parts of the anatomical joint, in particular maximum ranges of motion of key movements, to be taken into account. A suitable orientation both for positioning the artificial joint cavity and for positioning the artificial shaft implant is preferably determined and taken into account when planning the surgical operation. Since the orientation of the shaft implant and the joint cavity are related to each other, determining the orientation for both parts of the artificial joint can prevent a part, in particular the shaft implant, from being sub-optimally positioned, and in particular can prevent a restricted range of motion.

The range of motion of the hip joint can be determined intra-operatively, in order to then use the obtained data when planning an orientation for implanting the joint cavity and/or the shaft implant. In order to determine the suitable orientation for implanting the artificial joint, the following two analysis concepts can be used, which can also be combined with each other.

According to one concept, the maximum ranges of motion of key movements are determined, wherein said movements, for example, can be flexion/extension movements, an internal/external rotation or an adduction/abduction movement or other combined movements, such as for example an internal rotation during a flexion movement. In accordance with another concept, a direction of the movement that is critical for a dislocation (luxation) forms the basis. If the range of motion of an anatomical joint is analyzed, data are preferably obtained that can be used in at least one of the aforesaid concepts, such that the obtained data can be used to determine a suitable location for a joint cavity and/or a shaft implant, and this can be used to plan an implantation of the artificial joint on this basis. A surgeon then can position the joint cavity and/or shaft implant at the determined suitable position on the basis of the planning, in particular by using a navigation system in which marker means, for example, are attached to the parts of the artificial joint and/or to the body structures in which the parts of the artificial joint are to be implanted. The marker means are preferably detected by the navigation system and used to determine the location of the parts of the artificial joint. The location of the parts of the artificial joint can be determined relative to the aforesaid body structures, so as to provide the surgeon with valuable information concerning the location, in particular the relative location, of the body structures involved and of the artificial joint, during the operation.

A registration method that can be performed, for example, with the aid of a detection means that detects marker means, and in particular with the aid of a navigation system that comprises at least one of the following registration steps:

- a) A marker means (for example a reference star) is attached to the pelvis and/or to the femur in order to detect the location of the pelvis and/or the femur and in particular to track the movement of the location of the pelvis and/or the femur.
- b) The location of an ASIS point is detected, for example with the aid of a pointer. Alternatively or additionally, a point on the pubic bone can be detected, for example by means of a pointer. A pointer is a pointing device to which at least two marker spheres are attached and for which the relative location between the tip of the pointer and the marker spheres is known, such that landmarks and in particular points can be tapped using the tip and their location can be detected by means of a detection means, in particular by a navigation system, and thus registered, by detecting the marker spheres.
- c) The patient's leg is placed in a neutral location. This position of the femur relative to the pelvis is stored as a neutral location.
- d) Landmarks on a thigh and/or geometric properties that characterize the thigh, such as for example symmetry planes or symmetry axes, the axis of the shaft of the femur or the axis of the femoral neck, can be determined using marker means, pointers and/or diagnostic means (such as CT or x-ray recordings).
- e) The range of motion of the femur, in particular relative to the pelvis and/or in a predetermined reference system (examples of which have already been given above), is determined. It is in particular determined for a predetermined anatomical situation, such as for example the maximum flexion, maximum extension, maximum abduction, maximum adduction and for combined movements.
- f) Surface points of the acetabulum (hip joint cavity) are detected.

The steps mentioned in b) can be used to provide a scaled pelvic model. The steps mentioned above in c) can be used to define an initial or zero situation. This initial situation then can be used in order to serve as a reference point for key movements (such as for example a flexion movement, extension movement, adduction movement or abduction movement). The initial situation can serve as a reference point for the perimeters of the maximum range of motion. The initial situation is also preferably stored and can serve to determine the length of the leg and to calculate an offset.

Point e) above can also be supplemented by the following optional feature. The detected range of motion can be validated by plausibility tests. One example of this is a minimum acceptable and/or normal flexion range, such as normally obtains in a human being. The minimum flexion range which is still acceptable can for example be 110 degrees. Warning indications can indicate to an operator that the aforesaid plausibility criteria have not been met, e.g., if a flexion range is found to be less than 110 degrees.

The method and device in accordance with the invention, and in particular a program which, when it is executed on a computer or is loaded on a computer, performs the method in accordance with the invention, can be configured such that it assists the operator when he detects or supplements the anatomical data. The operator (for example a surgeon) can be assisted by the program when he has not yet completely and/or sufficiently detected the range of motion of the anatomical joint. On the basis of statistical models, the program can assist the operator in completing incomplete body structure data, such that the possible movements, preferably ranges of key movements, are in particular detected.

Accordingly, a suitable orientation for the artificial joint or a part of it, for example the joint cavity, is preferably calculated on the basis of at least one of the following two analysis concepts:

- a) maximum range of key movements;
- b) critical direction for a dislocation (luxation).

The above two concepts can be directed to positioning the joint cavity with a suitable orientation in a first step. However, since the implantation of the joint cavity and the implantation of the shaft implant are related to each other, complete planning preferably also comprises determining a suitable orientation of the shaft implant. While the orientation of the joint cavity can be specified relative to the patient's median sagittal plane, for example, the orientation of the shaft implant (in particular the shaft part of the shaft implant), for example, can be specified relative to a longitudinal axis of the femur. Once a suitable orientation for the joint cavity has been determined, a suitable corresponding orientation of the shaft implant can be determined on this basis to ensure the desired range of motion of the joint after the implantation. The method is preferably configured such that after one part of the artificial joint, e.g., the joint cavity, has been implanted, the orientation of the implanted part is verified and in particular measured. If the measured orientation does not match, e.g., it deviates somewhat from the orientation previously determined in accordance with the invention, then the previously made calculation can be recalculated or updated on the basis of the measured orientation. Determining the suitable orientation for the second implanted part of the artificial joint can thus be adapted to the actual orientation of the part of the artificial joint implanted first. This can ensure, despite deviations, that the range of motion of the artificial joint includes the range of motion of the anatomical joint. It is also possible to determine the orientation of the shaft implant first and to then determine the orientation of the joint cavity in a second step. The orientation of the shaft implant can in particular be verified after it has been implanted in the thigh, and the verified (i.e., measured) orientation can then be taken as a basis for calculating the suitable location for the joint cavity. It is also possible to implant the shaft implant first and verify its orientation, and then implant the joint cavity.

Figure 1B:
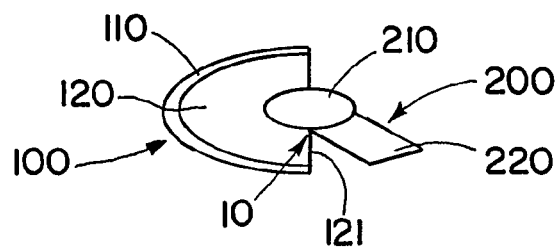
Figure 1C:
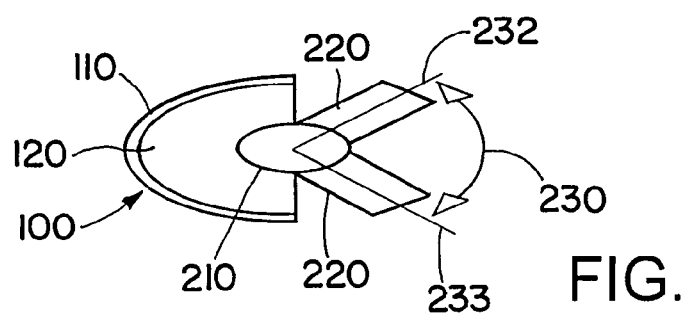

The following is also presented with regard to the analysis concept referred to above as a). Software executed by a processor can advantageously calculate the maximum ranges of key movements, for example the ranges of flexion/extension movements and abduction/adduction movements. These ranges then can be used to select and/or determine the best possible combination of a joint cavity and a joint head. Available combinations are advantageously provided by a database. FIGS. 1a-1c show an example of a combination of a first and second part of an artificial joint 100, 200 that provides a maximum range of a movement along a primary arc 230 (a so-called "primary arc range") of 100 degrees. The joint cavities 100 are preferably implanted, i.e., placed in a location, such that the maximum range can be achieved without an abutment 10. An "abutment" 10 means here that within the framework of a joint movement, a part 200 of the artificial joint abuts such that the joint movement is prevented from continuing further. An initial location or zero location of the artificial joint 100, 200 is thus preferably positioned such that it is in the middle of the maximum range or maximum ranges of the anatomical joint. FIG. 1a shows the artificial joint 100, 200 in such an initial position. FIG. 1b shows a situation in which the perimeter of a range of motion has been reached, e.g., a part 200 of the artificial joint is abutting against another part 100 (121) within the framework of a joint movement. More specifically, the transition area between the ball 210 of the joint and the shaft 220 of the joint abuts the end area 121 of the joint cavity 100 at the point 10. The joint cavity 100 consists of an outer cup 110 into which a lining 120 (also called "liner") is fitted. FIG. 1c shows a maximum range of motion 230 (primary arc range) that is defined by the points 10 of abutment and can for example be 100 degrees. An example is presented in the following:

The maximum flexion in the range with respect to the initial position is for example 80 degrees. The maximum extension compared to the initial situation is 15 degrees. This results in a maximum flexion/extension range of 95 degrees. Since this range of 95 degrees is smaller than the maximum range of motion of 100 degrees (primary arc range of 100 degrees) of the artificial joint of FIGS. 1a-1c, this artificial joint can be used. The middle of this maximum flexion/extension range is accordingly 47.5 degrees. This middle describes, in one plane, the suitable orientation for positioning the joint cavity with regard to the flexion/extension plane. If this suitable orientation is calculated in relation to the initial situation (zero situation), this would correspond to an orientation which corresponds to at least 32.5 degrees flexion. This also can be calculated from the median value of the maximum flexion/extension range of 47.5 degrees, minus the maximum extension range of 15 degrees.

Figure 2:
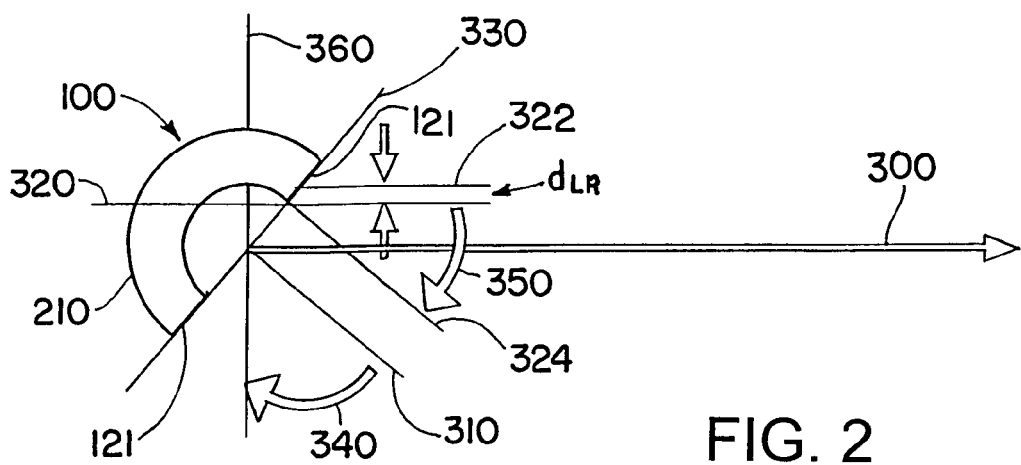
FIG. 2 illustrates a luxation resistance.

The following is also presented with regard to the aforementioned analysis criterion b). It is assumed that data are obtained that describe the maximum abduction. A program or the method in accordance with the invention, for example, can use these data and calculate, on this basis, the direction of a luxation that is possible in this case, wherein it is assumed that the luxation occurs along the femoral neck axis of the femur. The femoral neck axis can be determined from given anatomical data, such as can be ascertained, for example, by a computer tomogram (CT). The positional relationship between the maximum abduction location and the femoral neck axis is thus known. Preferably, it can also be assumed that in the case of a luxation, no abutment obtains between the first and second part of the artificial joint (in this example, between the head and the cavity). The geometric data, in particular data concerning the shape and/or configuration of the artificial joint, are preferably also known from a database. It may also be assumed that a part of the artificial joint, for example a center axis of the joint cavity, and the direction of the luxation enclose an angle that in the following is called the inclination angle. A mechanical resistance against the luxation depends on a distance that in the following is called the luxation parameter $d_{LR}$. This resistance depends on the inclination angle. This is illustrated in more detail in FIG. 2. FIG. 2 shows the joint cavity 100 in which there is a hemispherical opening for the head 210 of a joint head. When connected to the joint cavity 100, this joint head 210 can detach from the joint cavity 100. This is referred to as luxation. The direction of the luxation is indicated as 300 in FIG. 2. Different directions may be assumed for this luxation direction. Preferably, directions are assumed such as result for key locations of one part of the joint relative to the other part. The luxation direction, for example, can be determined for the state of maximum abduction. In particular, the luxation direction for this location or for other key locations and/or locations can be calculated such that it is assumed that a luxation occurs along the femoral neck axis. Thus, in the case of maximum abduction, the luxation direction can be identical to the femoral neck axis.

The geometric data for the artificial joint, in particular for an artificial joint selected from a plurality of artificial joints, are preferably known, e.g., stored in a database. The symmetry axis about which the joint cavity 100 of FIG. 2 is rotationally symmetrical is indicated by the reference sign 310 in FIG. 2. This centre axis 310 passes through the center point of the cup-shaped recess in the joint cavity 100 and is in particular perpendicular to a plane 330 that connects the end areas 121 of the joint cavity 100. The center axis 310 corresponds to the orientation of the artificial joint.

A so-called luxation axis 320 is parallel to the direction of the luxation 300. The axis 320 also is perpendicular to a straight line 360, which is perpendicular to the direction of the luxation 300 and passes through the median sagittal plane (from head to foot). The assumed luxation direction is perpendicular to it. In the state of maximum abduction, the luxation direction corresponds to the femoral neck axis. The straight line 360 intersects an intersection point between the center axis 310 and the plane 330. The luxation axis 320 also intersects the plane 330 at a perimeter point on the end area 121 of the joint cavity 100, namely the perimeter point on the end area 121 that is nearest to the center axis 310. The angle between the center axis 310 and the straight line 360, which is perpendicular to the luxation axis 320, is the inclination angle of the joint cavity 100 and is indicated as 340 in FIG. 2. The luxation inclination angle 350 is also indicated in FIG. 2 and is the angle between the luxation axis 320 and a straight line 324, which is perpendicular to the plane 330 and intersects the plane 330 at the aforementioned perimeter point on the end area 121.

The overlap between the edge of the implant and the highest point on the implant cavity (in a corresponding case) is referred to in the following as the luxation parameter $d_{LR}$ and results in the mechanical resistance offered to the luxation. In this example, the luxation parameter is specified by the distance $d_{LR}$, wherein the resistance resulting from this distance is increases as the distance increases. The distance $d_{LR}$ is the distance between the luxation axis 320 and a straight line 322 parallel to the axis 320. This parallel straight line 322 intersects the straight line 360, which is perpendicular to the luxation axis 320 and intersects the plane 330 in the middle between the end areas 121.

When determining the value of the needed luxation parameter, it is possible, in addition to geometric properties of the artificial joint, to also incorporate material properties of the artificial joint, in particular the surface friction properties and elasticity of the material. The more elastic and/or flexible the material of the artificial joint is, the easier it is for a luxation to be caused. The to smaller the friction between one part of the artificial joint and the other part of the artificial joint, e.g., between the joint head and the joint cavity, the easier it is for one part to be separated from the other part.

The luxation parameter $d_{LR}$ and consequently, as outlined above, the inclination angle of the luxation can be optimized in accordance with the invention such that a maximum abduction is enabled, wherein there is no abutment of one part of the joint against the other, and wherein a maximum resistance against a luxation is also ensured.

Once the optimum resistance (in particular the resistance resulting from the geometric properties) has been found, a luxation inclination angle 350 is thus determined. From the luxation inclination angle 350, a suitable inclination angle 340 of the artificial joint cavity and thus a suitable orientation of the artificial joint which corresponds to this inclination angle can be determined. The luxation direction can be determined at maximum abduction. The alignment of the body structures of the pelvis and the femur in this position are known. The minimum luxation parameter $d_{LR}$ needed in order to not dislocate is known, for example, from the database. This minimum luxation parameter $d_{LR}$ provides an inclination angle between the center axis 310 of the artificial joint and the luxation axis. For example, the luxation axis corresponds to the femoral neck axis, or the relationship between the luxation axis and the femoral neck axis is known (for example because the joint head has already been implanted). Using the femoral neck axis and the inclination angle, it is then possible to ascertain a suitable location of the center axis 310 and thus a suitable orientation of the joint cavity implant.

Figure 3:
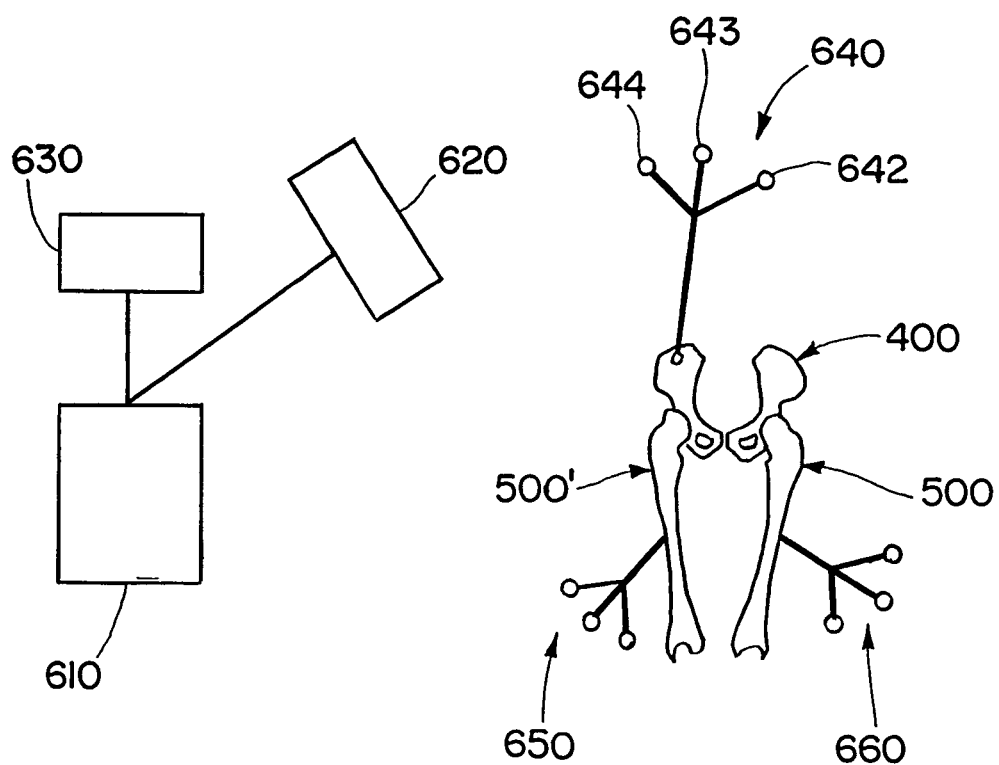
FIG. 3 schematically shows a set-up of a device in accordance with the invention.

FIG. 3 shows an exemplary device in accordance with the invention. A data processing means 610 is connected to a monitor 630 and to a detection means 620. The detection means 620 is designed to detect marker means 640, 650 and 660, which comprise three spheres indicated as 642, 643 and 644.

The marker means are attached to the pelvis and to each femur. If the femur 500 or 500' is moved relative to the pelvis 400, then possible locations of the femurs 500 and 500' relative to the pelvis 400 can thus be detected. In particular, typical key locations and extreme locations (maximum locations) on the patient can be detected, for example, during the operation and before an implantation is performed.

An artificial joint, for example a joint cavity and a joint head, then can be implanted on the basis of the detected data. The artificial joint, in particular each part of the artificial joint, also can be provided with a marker means in order to ensure that it is positioned exactly and as desired. The device can be designed to indicate to the surgeon the location relative to the pelvis 400 that the femur 500 or 500' still has to be placed to have sufficient data material for calculating a suitable location of the artificial joint. The means 610, 620 and 630 also can be used to position the artificial joint after the suitable orientation has been determined and in particular in accordance with the result of the planning method in accordance with the invention. This can be achieved by guiding the surgeon with indications and/or by controlling an implantation robot.

As discussed above, a preferred embodiment of the device in accordance with the present invention is one in which ratios of the flexion to the extension and of the abduction to the adduction are formed so as to determine a suitable orientation of the artificial joint. The suitable orientation of the artificial joint also can be determined using such a ratio.

It may be assumed that the following body structure data which describe the mobility of the anatomical joint have resulted from measuring or from a statistical analysis of a plurality of anatomical joints:
flexion=120 degrees;
extension=10 degrees;
abduction=40 degrees;
adduction=20 degrees.

These absolute angular values can be determined relative to the neutral location of the leg relative to the pelvis. The neutral relative location can be detected with the aid of reference stars on the femur and on the pelvis, wherein it is defined such that the femur is not rotated in the neutral relative location (no inner rotation or outer rotation) and such that the leg is aligned along an axis, preferably the mechanical axis of the leg. The mechanical axis is the axis in which the force acts when a person is standing. The neutral relative location can thus be detected in a simple way. The mechanical axis of the leg, for example, can be defined in medicine such that when a person is standing on both legs, the axis passes from the center of the hip bone, through the center of the knee, to the center point of the ankle and in particular exhibits an angle of three degrees to the vertical. The neutral relative location also can be determined by tapping landmarks. In order to determine the neutral relative location, even without measuring landmarks, the leg can simply be aligned along the mechanical axis. The relative location between the femur and the pelvis can be detected and stored. The neutral relative location is preferably measured by the device shown in FIG. 3, and preferably stored in memory. The neutral relative location is preferably also a constituent of the body structure data, in particular when only angular ratios and not absolute angular values are a constituent of the body structure data.

The above absolute angular values fulfil the following angular ratios:
flexion/extension=120 degrees/10 degrees=12/1
abduction/adduction=40 degrees/20 degrees=2/1.

In accordance with a preferred embodiment, the above angular ratios (in the example, 12/1 and 2/1) are then sufficient to precisely and unambiguously determine the position (orientation) of the joint when proceeding from a neutral relative location of the leg. The neutral relative location is preferably a relative location which can easily be determined, for example the standing leg as discussed above.

The following steps can for example be performed for planning (virtual) or an operation (actual):
a) The leg can be virtually or actually placed in the neutral relative location. This can be performed virtually, since the location data of the leg for the neutral relative location have been previously stored, as described above. These location data for the neutral relative location can be detected at the beginning of the operation, in particular by means of reference stars (e.g., by aligning the leg along the mechanical axis). The location data can be provided to a data processing system for planning.
b) The relative location of the femur relative to the pelvis, e.g., the neutral relative location, can be actually or virtually maintained. This means that the data that describe the neutral relative location are kept constant. The relative location between the parts of the joint, however, may be changed, e.g., the cavity implant is moved (actually or virtually) relative to the pelvis, while the femur and in particular the shaft implant or femoral neck axis is stationary, in order to change the relative location of the femoral neck axis or the neck axis of the shaft implant relative to the axis of the cavity implant until the desired angular ratios for the neutral relative location result.

The neutral axis corresponds to the centre axis 310 and thus to the orientation of the cavity implant (e.g., of the joint). The plane via which the acetabulum joint is open, e.g., the plane 330, theoretically has an aperture angle of 180 degrees and is divided uniformly by the neutral axis into 90 degrees and 90 degrees. Thus, this results in a ratio of 1/1 for the neutral relative location of the cavity implant. The reference axis (e.g., the femoral neck axis of the neck axis of the shaft implant), for example, can (but need not) be planned and in particular verified. Thus, initially and purely optionally, the center/neutral axis of the acetabulum implant can be aligned with the reference axis. This then results in "range of motion" ratios of 1/1. Proceeding on this basis, it is then possible to move the cavity implant until the desired angular ratio in the neutral relative location has been achieved.

Setting the angular ratios can be realized by the following two steps:

a) In order to obtain the desired ratios, one part of the joint (for example the acetabulum implant) can be moved or rotated, while for example the other part of the joint (e.g., the femur implant) remains stationary. Moving or rotating the cavity implant causes a change in the flexion/extension direction. The cavity implant is moved or rotated such that the desired ratio is achieved (e.g. 12/1 for the flexion/extension=166.15 degrees/13.85 degrees). After the movement or rotation, the open plane of the part of the joint (the acetabulum implant) can be divided by the reference axis in the desired ratio. Thus, after the movement or rotation, the open plane of the part of the joint (the acetabulum implant) can be divided by the femoral neck axis or the neck axis of the implant in the desired ratio (if the leg is in the neutral relative location) since the neutral axis of the part of the joint (the center axis) is also rotated when the part of the joint is rotated. The reference axis for dividing can be the femoral neck axis or the neck axis of the implant, which has for example been determined by planning and/or verifying.

b) The open plane of the joint is preferably divided for at least two determined angular ratios, e.g., in addition to the flexion/extension, also for the abduction/adduction. To this end, an additional step can be performed. In the cited example, the ratio x/y, for example 2/1, would then be obtained in a second step for the abduction/adduction, e.g., the open plane of the acetabulum implant would thus be sub-divided in the abduction/adduction direction by the reference axis in a ratio of x/y, for example 2/1 or 120 degrees/60 degrees. In this way, a plurality of ratios can be incorporated into optimizing the position of the cavity implant.

The aforesaid steps can be performed within the framework of a planning method. Marker means are preferably attached to the first and second body structure (for example, the femur and acetabulum). Thus, with the aid of planning in accordance with the invention, the desired angular ratio or ratios can be monitored by the surgeon and set by means of the device in accordance with the invention. Alternatively, the suitable orientation also can be verified without detecting the location of the reference axis using pointers or markers. This can be accomplished by moving the first and second body structures relative to each other and verifying whether the desired ratios result after the implantation. If not, a correction can be made.

Instruments with markers can be used to position the implants. This then enables the implants to be inserted in the way provided for in the planning. After the implants have been inserted, a range of motion analysis can also be performed, in which the two body structures can be moved relative to each other. This then provides the movements (for example flexion, extension, . . . ), and the result of the operation and the planning can be compared.

Figure 4:
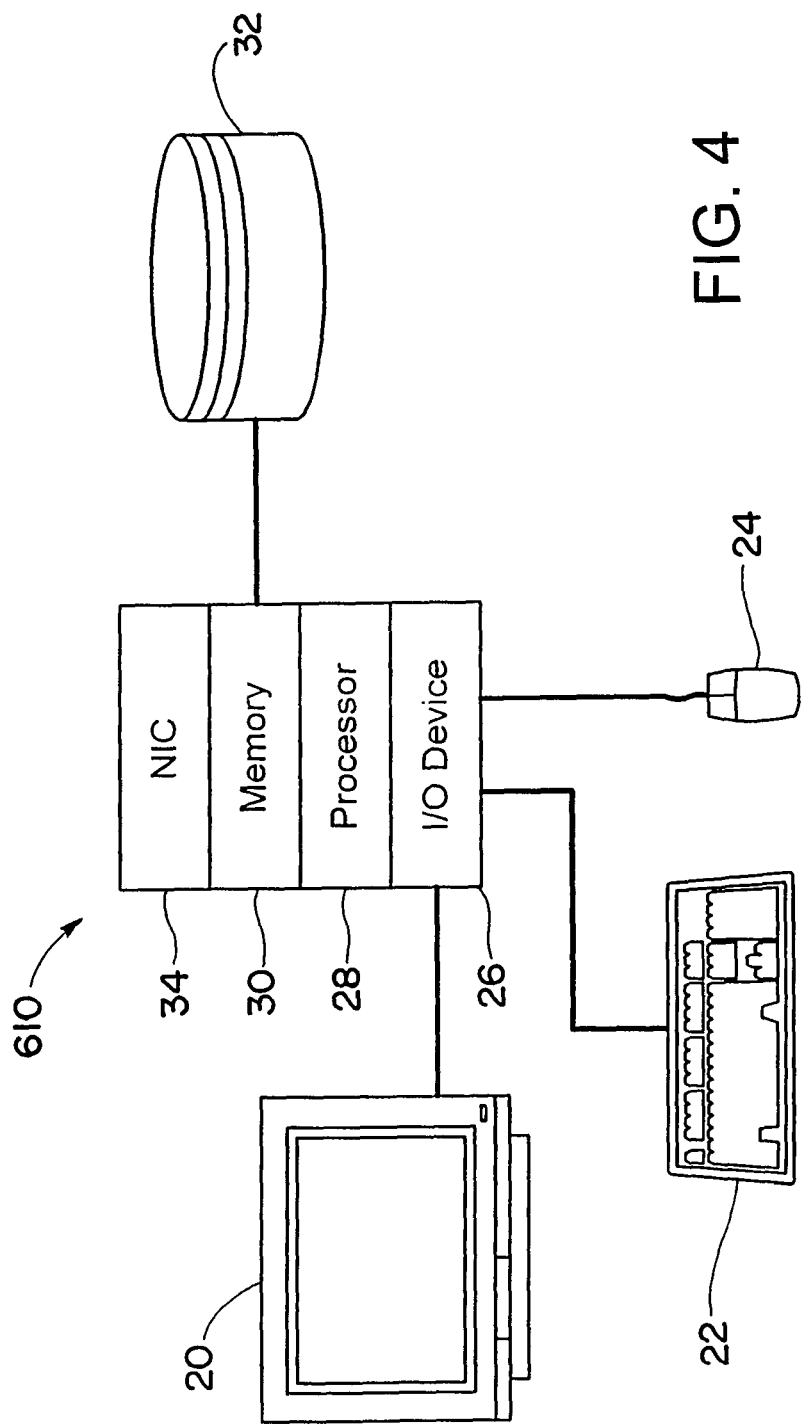
FIG. 4 is a block diagram of an exemplary computer system that may be used to implement the method in accordance with the invention.

Moving now to FIG. 4 there is shown a block diagram of an exemplary processing device 610 (e.g., a computer) that may be used to implement the method described herein. The computer 610 may include a display 20 for viewing system information, and a keyboard 22 and pointing device 24 for data entry, screen navigation, etc. A computer mouse or other device that points to or otherwise identifies a location, action, etc., e.g., by a point and click method or some other method, are examples of a pointing device 24. Alternatively, a touch screen (not shown) may be used in place of the keyboard 22 and pointing device 24. The display 20, keyboard 22 and mouse 24 communicate with a processor via an input/output device 26, such as a video card and/or serial port (e.g., a USB port or the like).

A processor 28, such as an AMD Athlon 64® processor or an Intel Pentium IV® processor, combined with a memory 30 execute programs to perform various functions, such as data entry, numerical calculations, screen display, system setup, etc. The memory 30 may comprise several devices, including volatile and non-volatile memory components. Accordingly, the memory 30 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 28 and the memory 30 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database 32. The storage medium may be a hard drive, for example, or any other storage means that can retain data, including other magnetic and/or optical storage devices. A network interface card (NIC) 34 allows the computer 610 to communicate with other devices.

A person having ordinary skill in the art of computer programming and applications of programming for computer systems would be able in view of the description provided herein to program a computer system 610 to operate and to carry out the functions described herein. Accordingly, details as to the specific programming code have been omitted for the sake of brevity. Also, while software in the memory 30 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A method for determining an orientation of an artificial joint in a human or animal body, wherein a first part of the artificial joint and a second part of the artificial joint are designed to form an artificial joint connection with each other, the first part provided for implantation in a first body structure of the human or animal body, and the second part provided for implantation in a second body structure of the human or animal body, the first and second parts replacing an anatomical joint that connects or connected the first body structure to the second body structure (500), comprising:

before replacement of the anatomical joint, obtaining body structure data that describe a mobility of the first body structure relative to the second body structure, the first body structure and the second body structure being connected by the anatomical joint and the mobility including information concerning at least one of a plurality of possible relative movements of the first body structure relative to the second body structure or a plurality of possible relative locations of the first body structure relative to the second body structure; and based on the body structure data, determining, with computer assistance, an orientation of the first and second part of the artificial joint for planning an orientation of the artificial joint that is suitable for implantation.

2. The method according to claim 1, wherein obtaining body structure data includes obtaining body structure data that describes the mobility by at least one first angular ratio that follows from a ratio of a first angle to a second angle, wherein the first angle and second angle are determined by a first movement of a first part of the anatomical joint to be replaced relative to a second part of the anatomical joint to be replaced, and wherein the first movement is performed in a first direction and/or in a first plane from a first movement end point to a second movement end point, and the first angle is the angle between the first movement end point and a predefined neutral relative location between the two movement end points, and the second angle is the angle between the second movement end point and the neutral relative location.

3. The method according to claim 2, wherein describing the mobility further includes describing the mobility by at least one second angular ratio that follows from a ratio of a third angle to a fourth angle and is determined by a second movement in a second direction and/or second plane that is at least oblique with respect to the first direction and/or plane, wherein the second movement is performed from a third movement end point to a fourth movement end point, and the third angle is the angle between the third movement end point and the predefined neutral relative location between the two movement end points, and the fourth angle is the angle between the fourth movement end point and the neutral relative location.

4. The method according to claim 3, wherein the second direction and/or second plane is orthogonal to the first direction or plane.

5. The method according to claim 2, further comprising performing the first and/or second movement over the entire anatomically possible range of motion.

6. The method according to claim 2, further comprising determining the neutral relative location by detecting landmarks on the first and second body structure, wherein the landmarks assume a predetermined relative location in the neutral relative location.

7. The method according to claim 1, wherein the describing the mobility includes determining the mobility based on a ratio of a flexion angle to an extension angle of the artificial joint and/or based on a ratio of an abduction angle to an adduction angle of the artificial joint.

8. The method according to claim 1, further comprising providing at least one implant dataset relating to the mobility of the first part relative to the second part, wherein the suitable orientation of the artificial joint is determined based on the body structure data and the at least one implant dataset.

9. The method according to claim 8, wherein the implant dataset comprises at least one of:
at least one possible range of motion of the at least one anatomical joint;
possible locations of the first part relative to the second part;
data concerning the geometry of the anatomical joint; or
data ($d_{LR}$) relating to the inhibition of or a resistance against a relative movement of the first and second part.

10. The method according to claim 1, wherein the body structure data that describe the mobility comprises at least one of:
at least one range of motion that is possible using the anatomical joint to be replaced or using an identical joint;
data concerning a geometry of the anatomical joint;
data concerning an inhibition of or a resistance against a relative movement of the first and second body structure; or
data concerning at least one luxation direction.

11. The method according to claim 10, wherein determining the orientation suitable for implanting the artificial joint is embodied such that when the artificial joint is positioned with the suitable orientation, a possible range of motion of the anatomical joint is included in the possible range of motion of the artificial joint.

12. The method according to claim 1, wherein determining the orientation suitable for implanting the artificial joint is embodied such that a resistance against a luxation of the artificial joint is optimized and/or the resistance is used to determine the suitable orientation or to assess and/or improve an orientation that has already been determined to be suitable.

13. The method according to claim 1, further comprising verifying the anatomical data by comparing the data with predetermined data that represent normal anatomical or maximum possible mobilities and/or possible relative locations of the body structures in a human being or an animal.

14. The method according to claim 1, wherein the at least one implant data set comprises a first implant data set and a second implant data set, wherein the first implant data set describes a first artificial joint, and the second implant data set describes a second artificial joint, and based on the body structure data and the first and second implant datasets, at least one suitable artificial joint is selected and the at least one suitable orientation for implanting the at least one selected artificial joint is determined.

15. The method according to claim 1, wherein obtaining body structure data includes at least partially determining the body structure data via a navigation system, a detection device, a medical analysis and/or a diagnostic device.

16. The method according to claim 1, wherein obtaining body structure data includes:
attaching at least one marker device to the first and/or second body structure; and
detecting a location and/or a movement of the first and/or second body structure by detecting the at least one marker device.

17. The method according to claim 1, further comprising using the determined suitable location for implanting the artificial joint to plan the implantation of the artificial joint in a human body.

18. A computer program embodied on a non-transitory machine readable medium for determining an orientation of an artificial joint in a human or animal body, wherein a first part of the artificial joint and a second part of the artificial joint are designed to form an artificial joint connection with each other, the first part provided for implantation in a first body structure of the human or animal body, and the second part provided for implantation in a second body structure of the human or animal body, the first and second parts replacing an anatomical joint that connects or connected the first body structure to the second body structure, comprising:
code that before replacement of the anatomical joint, obtains body structure data that describe a mobility of the first body structure relative to the second body structure, the first body structure and the second body structure being connected by the anatomical joint and the mobility including information concerning at least one of a plurality of possible relative movements of the first body structure relative to the second body structure or a plurality of possible relative locations of the first body structure relative to the second body structure; and
code that based on the body structure data determines a suitable orientation of the first and second part of the artificial joint for planning an orientation of the artificial joint that is suitable for implantation.

19. A device for determining an orientation that is suitable for an implantation of at least one artificial joint in a human or animal body, wherein a first part of the artificial joint and a second part of the artificial joint are designed to form an artificial joint connection with each other, the first part being provided for implantation in a first body structure of the human or animal body, and the second part being provided for implantation in a second body structure of the human or animal body, the first and second parts replacing an anatomical joint that connects or connected the first body structure to the second body structure, comprising:
a memory for storing body structure data that describe a mobility of the first body structure relative to the second body structure, the first body structure and the second body structure being connected by the anatomical joint and the mobility including information concerning at least one of a plurality of possible relative movements of the first body structure relative to the second body structure or a plurality of possible relative locations of the first body structure relative to the second body structure; and
a data processing device configured to determine an orientation of the anatomical joint and/or to determine, based on the body structure data, a suitable orientation of the first and second part of the artificial joint for planning an orientation of the artificial joint that is suitable for implantation.

20. The device according to claim 19, further comprising a detection device for at least partially determining the body structure data, wherein the detection device is configured to detect a location and/or a movement of the first and/or second body structure by detecting at least one marker device attached to the first and/or second body structure.

21. The device according to claim 20, further comprising an indicating device configured to output, on the basis of stored locations and/or movements, the locations and/or movements of the first and/or second body structure that still have to be detected in order to obtain the body structure data needed to determine the orientation of the anatomical joint and/or the suitable orientation of the first and second part of the artificial joint.

* * * * *